United States Patent [19]

Reagen

[11] Patent Number: 5,777,735
[45] Date of Patent: Jul. 7, 1998

[54] IN SITU ANALYSIS APPARATUS

[75] Inventor: William K. Reagen, Stillwater, Minn.

[73] Assignee: Minnesota Mining and Manufacturing Company, St. Paul, Minn.

[21] Appl. No.: 723,433

[22] Filed: Sep. 30, 1996

[51] Int. Cl.$^6$ .................. G01B 9/02; G01N 1/10; G01N 21/01; G01N 21/00
[52] U.S. Cl. .................. 356/346; 356/244; 356/246; 356/440
[58] Field of Search .................. 356/346, 244, 356/246, 439–440

[56] References Cited

U.S. PATENT DOCUMENTS

| | | |
|---|---|---|
| 3,860,818 | 1/1975 | Stalder et al. |
| 3,989,938 | 11/1976 | Auth ........................ 356/346 |
| 4,657,390 | 4/1987 | Doyle ....................... 356/244 |
| 5,068,798 | 11/1991 | Heath et al. |
| 5,252,828 | 10/1993 | Kert et al. .............. 250/338.5 |
| 5,440,143 | 8/1995 | Carangelo et al. ........ 356/246 |

FOREIGN PATENT DOCUMENTS

| | | |
|---|---|---|
| 0 006 749 | 1/1980 | European Pat. Off. |
| 2 190 184 | 11/1987 | United Kingdom. |
| 2 281 967 | 3/1995 | United Kingdom. |

OTHER PUBLICATIONS

J. Hampel-Stephens et al., "Practical Experiences in Environmental Compliance Auditing for an Air Sampling Program", presented at the 85$^{th}$ Annual Meeting & Exhibition, Air & Waste Management Association, Kansas City, Missouri, Jun. 21–26, 1992 (pp. 1–11).

P. Hanst, "94 Catalog—Infrared Analysis, Inc.", pp. 1–24 (1994).

"MIDAC FTIR Air Monitoring System", brochure of MIDAC Corporation, Costa Mesa, CA, 6 pgs (1992).

"Protocol for the Use of Extractive Fourier Transform Infrared (FTIR) Spectrometry for the Analyses of Gaseous Emissions from Stationary Sources", U.S. EPA, *EMTIC Bulletin Board*, pp. 1–33 (3 Feb. 1995).

A. Wait et al., "Ensuring Environmental Data Quality", presented at the 85$^{th}$ Annual Meeting & Exhibition, Air & Waste Management Association, Kansas City, Missouri, Jun. 21–26, 1992 (pp. 1–11).

*Primary Examiner*—Frank G. Font
*Assistant Examiner*—Jason D. Vierra-Eisenberg
*Attorney, Agent, or Firm*—John A. Fortkort

[57] ABSTRACT

A gas analysis apparatus includes an optical source for providing an optical signal, an interferometer for modifying the optical signal, and an optical signal detector. A first housing having folded path optical elements positioned therein; the elements defining a sample path through which the optical signal passes from the interferometer to the optical signal detector. The first housing has a sample introduction opening. A second housing defines a sample holding volume. The second housing is sealingly positioned with respect to the first housing for fluidly connecting the sample path of the first housing with the sample holding volume of the second housing through the sample introduction opening. A recirculating flow may be provided between the sample path and the sample holding volume. The second housing may include an access port with a detachable access closure through which a material may be placed in the sample holding volume. A method for using the apparatus is also described.

8 Claims, 5 Drawing Sheets

IN SITU ANALYSIS APPARATUS

FIELD OF THE INVENTION

The present invention relates generally to gas analysis. More particularly, the present invention relates to spectroscopic in situ gas analysis apparatus and methods.

BACKGROUND OF THE INVENTION

The air quality, for example, in the workplace or at home, is important not only for complying with legislative permissible levels of various gases or chemical compounds, but also because of the potential health hazards that may be imposed by toxic or flammable gases. As a result, various air quality programs have been utilized for monitoring or analyzing air quality in various locations and/or analyzing the concentration of off-gases which are produced during or under certain circumstances. For example, a particular process in a factory may result in material off-gassing that may be a potential hazard. However, such off-gassing analysis is only as reliable as the quality of data achieved using currently available off-gas analysis systems and techniques. Conventional analysis of off-gases may include the use of environmental chambers for generating the off-gas, grab or extraction sampling of gases in the environmental chamber, and analysis using conventional Fourier transform infrared (FTIR) gas analysis systems.

Virtually all compounds absorb infrared energy. In FTIR monitoring, infrared energy passes through a sample area, acquiring a characteristic "fingerprint" of the chemicals present due to the unique set of wavelengths they absorb. Conventional off-gassing analysis techniques typically include FTIR extractive analysis systems with an environmental chamber for generating the off-gas samples. The off-gas samples are then extracted or grabbed and analyzed by the extractive analysis system. The extractive analysis system typically consists of a source of mid-infrared radiation, an interferometer, an enclosed sample cell of known absorption path length, an infrared detector, optical elements for the transfer of infrared radiation between components, and gas flow control and measurement components. Adjunct and integral computer systems and spectroscopic software are used for controlling the FTIR systems, for processing the signals detected by the infrared detector, and for performing both Fourier transforms and quantitative analysis of spectral data. These systems typically monitor many infrared wavelengths simultaneously, and pass on the information detected to the computer system, where it can be transformed into a spectrum. The spectroscopic software analyzes the spectral information. Multi-component analysis of the data can immediately determine which of a certain set of species are present, and how much of each species is present. Further, the spectrum can be analyzed to determine if any unexpected species were detected; identification of such species can also be made in many cases. The absorption spectrum of gases in a mixture of gases are described by a linear absorption theory referred to as Beer's law. Using this law, FTIR systems use the computerized analytical spectroscopic software to quantify compounds by comparing the absorption spectra of known (i.e. reference) gas samples to the absorption spectrum of the sample gas. Such systems normally store the data permanently on a storage media, such as disks, to record the results for use at later times.

Such extractive FTIR systems, available from MIDAC Corp., Costa Mesa, Calif., and others, which use an enclosed sample cell, can be calibrated effectively using known reference gases, i.e. calibration transfer standards and properly prepared spectral reference data. For example, a calibration transfer standard can be run through the enclosed sample cell resulting in an absorption spectrum that when compared to the standard's known spectrum under a different set of conditions can be utilized to calibrate the FTIR system.

The sampling and handling utilized with extractive FTIR systems, such as when the off-gas sample is grab sampled or extracted from the environmental chamber and then transported to an extractive analysis system, leads to less than desirable quality for the data resulting from the extractive analysis then performed. In addition, the grab sample may not be a representative sample of actual off-gas produced in the environmental chamber. For example, the off-gassing may tend to accumulate in a part of the environmental chamber other than the portion from which the off-gas sample is extracted. Further, the environmental chamber and the container utilized for transport of the gas sample from the environmental chamber to the extractive gas analysis system can affect the concentration levels of various compounds within such structures. For example, many compounds will react with the wall structures or may stick to wall structures of the transport container or environmental chamber such that when analysis is performed, accurate concentration levels are not in the sample path of the system and therefore, not effectively measured.

For the above reasons and reasons that will become apparent from the description below, improvements to gas analysis systems and methods for performing gas analysis for material off-gassing are needed. For example, there is a need for in situ gas analysis systems and methods that can perform near real time in situ material off-gassing analysis with the capability of detecting low chemical compound concentration levels without the need for extractive sampling.

SUMMARY OF THE INVENTION

A gas analysis apparatus of the present invention includes an optical source for providing an optical signal, and an optical signal detector. A first housing has folded path optical elements positioned therein. The optical elements define a sample path through which the optical signal passes from the interferometer to the optical signal detector. The first housing has a sample introduction opening. A second housing defines a sample holding volume. The second housing is sealingly positioned with respect to the first housing for fluidly connecting the sample path of the first housing with the sample holding volume of the second housing through the sample introduction opening.

In one embodiment of the apparatus, a recirculating flow is provided between the sample path and the sample holding volume.

In another embodiment of the apparatus, the second housing includes an access port with a detachable access closure. Further, the first housing may be a cylindrical enclosure having first and second ends for supporting the folded path optical elements with the sample introduction opening located in the cylindrical enclosure between the first and second ends.

A device for use in an optical analysis system is also described. The device includes a first housing having folded path optical elements positioned therein. The optical elements define a sample path through which an optical signal is passed. The first housing has a sample introduction opening. The device further includes a second housing defining a sample holding volume. The second housing is sealingly positioned with respect to the first housing for fluidly connecting the sample path of the first housing with the sample holding volume of the second housing through the sample introduction opening.

In one embodiment of the device, a recirculating flow is provided between the sample path and the sample holding volume.

A method of analyzing off-gases from a material in accordance with the present invention is also described.

BRIEF DESCRIPTION OF THE DRAWINGS

FIG. 2b is an illustration of part of the mirror configuration of FIG. 2a;

FIG. 2c is an alternative illustration of part of the mirror configuration of FIG. 2a;

FIG. 2d is an alternative illustration of part of the mirror configuration of FIG. 2a;

DETAILED DESCRIPTION OF THE EMBODIMENTS

Figure 1:
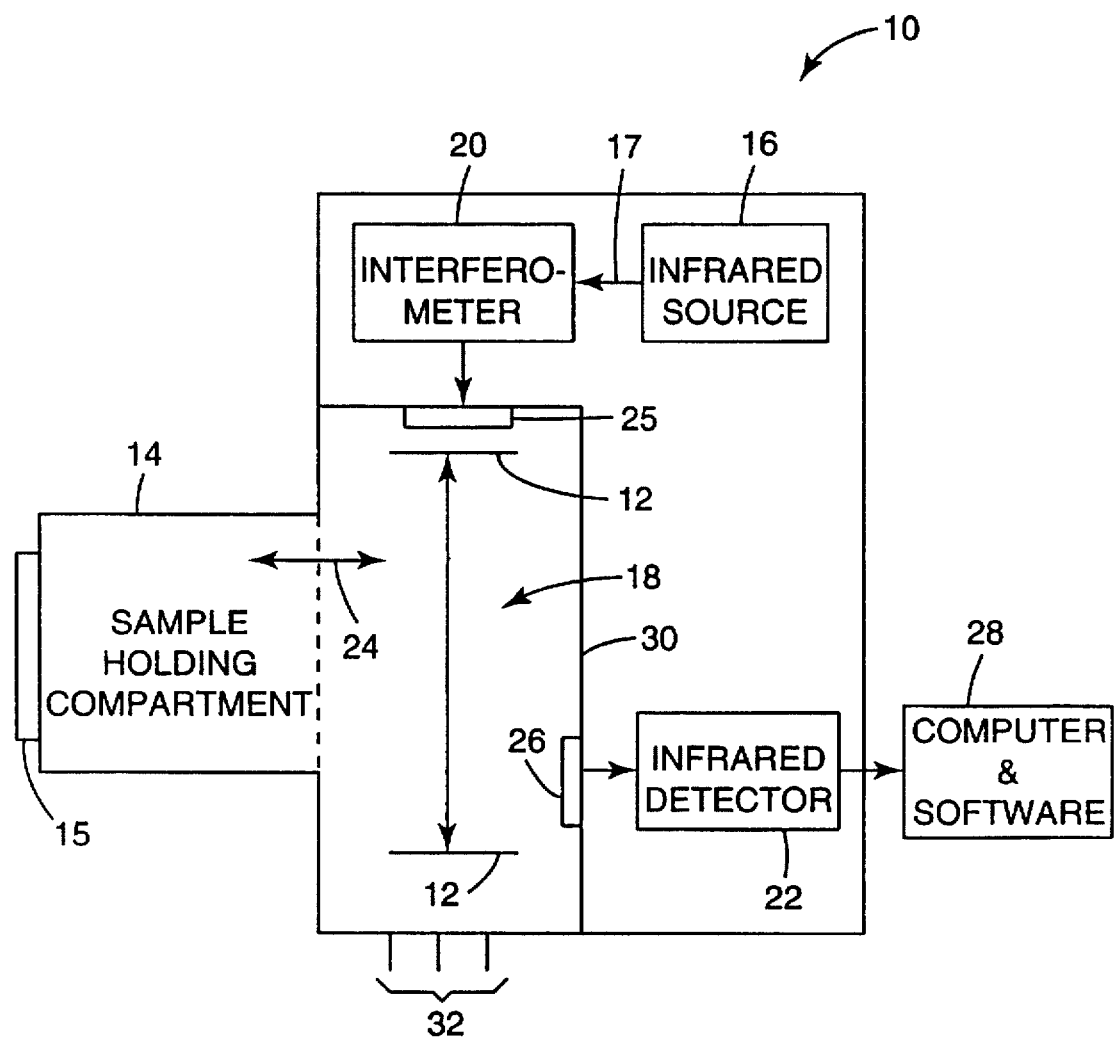
FIG. 1 is a block diagram of an in situ infrared spectrometry apparatus in accordance with the present invention.

The long term exposure of people to low levels of hazardous substances can have serious health consequences. Measurements of gaseous agents for compliance demonstrations and remediation efforts with regard to such hazardous substances are typically achieved with sample collection devices and subsequent laboratory analyses, i.e. extractive analysis systems, such as for analysis of material off-gases which may include the use of environmental chambers for generating the off-gas, grab or extraction sampling of gases in the environmental chamber, and analysis using conventional Fourier transform infrared (FTIR) gas analysis systems. However, in situ infrared absorption spectrometry provides more useful and cost effective measurements for off-gases than the typical "grab" sample technique (previously described in the Background of the Invention). The in situ infrared spectrometry apparatus 10, as shown in the block diagram of FIG. 1, allows for such in situ infrared absorption spectrometry producing high quality and highly reliable data by combining an environmental chamber with a spectrometry apparatus.

The in situ infrared spectrometry apparatus 10 provides the advantages of infrared absorption spectrometry to provide detection of low concentration levels through the use of a folded path optical mirror configuration 12, such as a White cell mirror configuration, which yields a large absorption path length. Yet further, the spectrometry apparatus 10 produces high quality, highly reliable, and near real-time results through the use of a sample holding compartment 14. The sample holding compartment 14 defines a sample holding volume into which one or more materials can be placed. Off-gassing of the material placed into the sample holding compartment is introduced in the sample path 18 defined by the folded path mirror configuration 12. The off-gases from the material may then be analyzed in situ. This is unlike the conventional extractive devices described in the Background of the invention, in which a grab sample is provided to a separate spectrometry system to perform the analysis of off-gasses collected, for example, from an environmental chamber.

The spectrometry apparatus 10 employs Fourier transform (FT) spectroscopic techniques, which provide extremely high signal-to-noise ratios, response times on the order of seconds to minutes, and large infrared bandwidth. Extractive FTIR systems have been proven extremely effective in measurements of molecular concentrations in complex gas mixtures, and FTIR methodologies for compliance air emission testing have been substantially defined, such as in the protocol, U.S. EPA, "Protocol for the Use of Extractive Fourier Transform Infrared (FTIR) Spectrometry for the Analysis of Gaseous Emissions from Stationary Sources," *EMTIC Bulletin Board* (3 Feb. 1995). Such extensive quality assurance and control procedures developed for extractive FTIR methods are directly applicable to the infrared spectrometry apparatus 10 as described herein and this protocol is incorporated herein in its entirety by reference.

The present invention shall now be described in further detail with reference to FIGS. 1 and 2. The in situ infrared spectrometry apparatus 10, as shown generally in the block diagram of FIG. 1, includes an infrared source 16 generating a light beam 17 in the infrared region, i.e. 0.78 to 800 micron wavelength of the electromagnetic spectrum, particularly in the mid-infrared region of approximately 4.0 to 50 microns. The light beam 17 is modulated utilizing an interferometer 20 as is known to one skilled in the art. For example, the interferometer 20 divides the light beam 17 into two or more paths using a beam splitter (i.e. such as a ZnSe beam splitter or any other known splitter), generates an optical path difference between the beams, and recombines them in order to produce repetitive interference maxima and minima as the optical path difference is varied. The modulated light beam from the interferometer 20 is transferred to the folded path optical mirror configuration 12 by various devices (not shown), including various transfer optics and laser alignment devices as are readily known to one skilled in the art. The modulated light beam is provided to the sample path 18, i.e. the sample volume defined by the folded path mirror configuration 12, through an optical window 25. The modulated light beam passes multiple times in the mirror configuration 12 prior to exiting the sample path 18 through another optical window 26 for transfer by additional optical elements, such as transfer optics (not shown) to an infrared detector, i.e. photo detector 22. The infrared detector 22 then provides data signals as is known to one skilled in the art to associated computer equipment 28. The optical windows may be any standard infrared window, e.g., NaCl windows.

The associated computer equipment 28 includes associated spectral data collection and spectroscopic analysis software and spectral reference data for quantifying compounds by comparing absorption spectral data of known (i.e. reference) gas samples to the absorption spectrum of the sample in the sample path 18, for example, a sample including off-gases from materials in the sample holding compartment 14. Such spectroscopic analysis software may include standard mathematical techniques used for such comparisons, such as classical least squares, inverse least squares, cross-correlation, factor analysis, partial least squares, and any other mathematical techniques used in conventional spectrometry analysis systems.

Most of the above elements, in general, are the typical components of extractive gas analysis systems, readily known to those skilled in the art. However, spectrometry apparatus 10 further includes sample holding compartment 14 including an access port 15 through which one or more materials may be positioned and analyzed. Off-gases from the materials in the sample holding compartment are introduced into the sample path by a recirculating flow (represented generally by arrows 24) between the sample holding volume defined by sample holding compartment 14 and sample path 18 such that a representative sample of off-gases is introduced into the sample path 18.

Figure 2A:
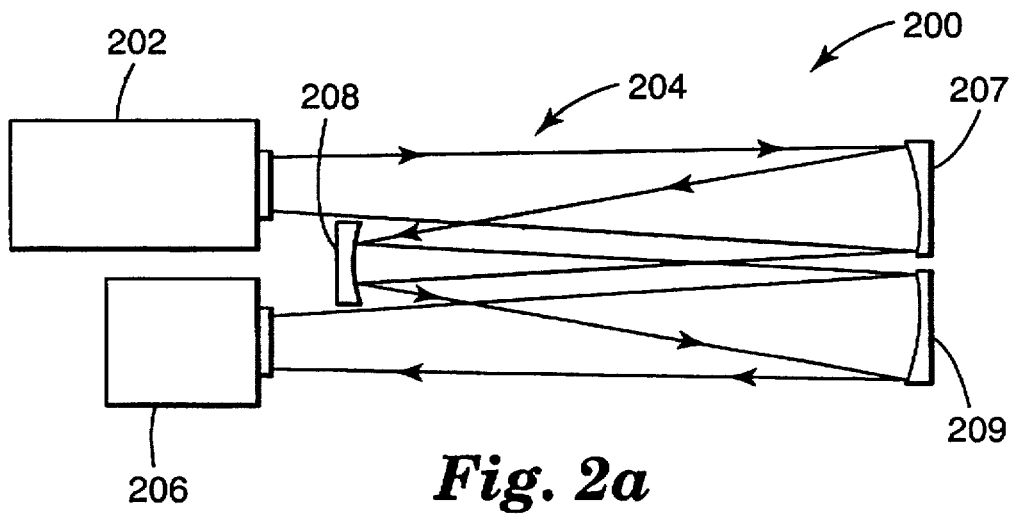
FIG. 2a is an illustration of a prior art White cell folded path optical mirror configuration.

For example, such elements other than those associated with the sample holding compartment 14, may be part of a conventional White cell as illustrated in FIG. 2a. The typical White cell 200 includes an interferometer source 202 for providing a modulated laser beam to folded path optical mirror configuration 204 which transfers the modulated light beam to a detection system 206 thereof. The folded path optical mirror configuration 204 generally includes three mirrors, including a field mirror 208 and two objective mirrors 207 and 209.

Figure 2B:
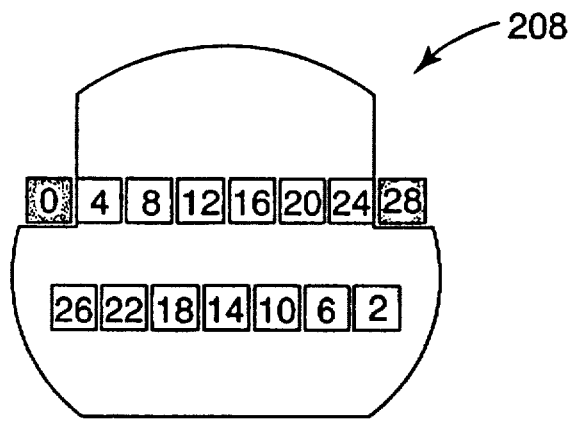

The field mirror 208 of a typical White cell mirror configuration is further shown in FIG. 2b. Reference shall be made with regard to the field mirror 208 to describe the operation of the cell utilizing the folded path optical mirror configuration 204. In operation of the White cell, the light from the interferometer source 202 is provided into the cell and through at least four passes. The light beam from the source 202 is initially focused into a real image in the entrance aperture of the cell. In FIG. 2b, this entrance aperture is designated the zero image. After passing through the zero image, the beam diverges and is collected by objective mirror 207. The objective mirror 207 is a spherical mirror situated two focal lengths from the image so that it refocuses the image, inverted, on the lower part of the opposite field mirror 208. The first image is marked "2" for two passes. The field mirror 208 is aimed so that the reflected diverging beam falls entirely on the second objective mirror 209. This is then aimed to form another image, marked "4" (FIG. 2b) about the central line of the field mirror 208 along side the zero image. If this image falls symmetrically opposite the first image (marked "2"), the beam will be returned to the first objective mirror 207 at the required small angle with the input beam, so that all the energy is again collected and returned and there will be at least four more passes through the folded path optical mirror configuration 204.

Figure 2C:
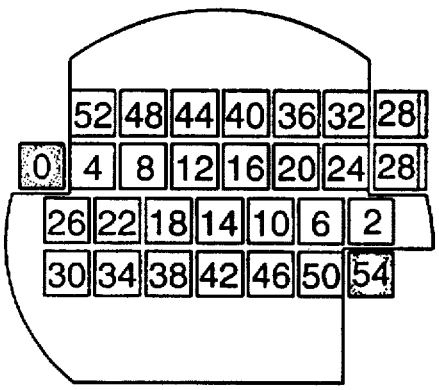
Figure 2D:
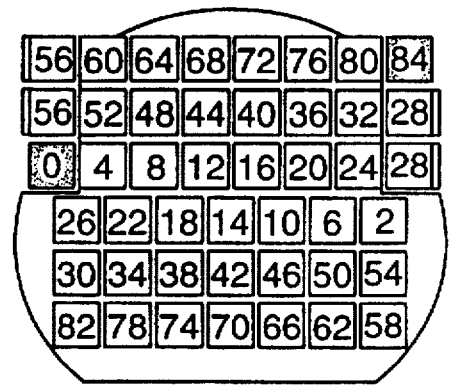

As shown in FIGS. 2c, modifications to the field mirror utilizing a retroreflecting pair of mirrors 28 at the normal exit port increases the amount of available mirror surface at the field mirror side of the cell. This allows the use of a more collimated light, thus increasing the energy throughput without enlarging the main collecting mirrors. Two additional rows of images double the number of passes by means of the retroreflective mirrors. This increased sample path length in turn provides lower detection limits for the gases in the sample path. Further, as shown in FIG. 2d, a second retroreflecting pair of mirrors 56 on the input side of the field mirror is added to create six rows of images. Again, this increases the sample path length and, in general, lowers the detection limits.

As would be readily apparent to one skilled in the art and as shown above, various alternative mirror configurations are possible along with various components that form the spectroscopic portions of the apparatus 10. The present invention utilizing the sample holding compartment 14 in conjunction with the folded path mirror configuration 12 that defines the sample path 18 of the apparatus 10, can be utilized with many different folded path mirror configurations and spectroscopic components. For example, the present invention including the sample holding compartment 14 can be used with any of the White cell mirror configurations 204 shown in FIG. 2 and any other folded path mirror configurations as described in the publication "Gas Analysis Manual for Analytical Chemists in Two Volumes - Volume 1 - Gas Measurement in the Fundamental Infrared Region", by Philip L. Hanst and Steven T. Hanst and in the 1994 Catalog "Infrared Analysis, Inc. - Specialists in the Measurement of Gases", each of which is entirely incorporated herein by reference. Such mirror configurations are available from Infrared Analysis, Inc., Irvine, Calif. Other mirror configurations incorporating folded optical paths are applicable (e.g., a Wilkes cell mirror configuration) and any other folded path mirror configuration of similar nature known to those skilled in the art may also be utilized in conjunction with the present invention.

Suitable multi-pass mirror configuration 12 requires only that the optics provide a long absorption path length to achieve low detection limits. The optical path length should be in the range of about 1 m to about 300 m, preferably about 80 m to about 200 m.

Further, any suitable spectrometry system and components thereof having a folded path mirror configuration that provides an optical path of suitable length can be utilized in conjunction with the present invention. For example, any suitable spectroscopic software and computer system that performs the system control, data processing of detected information, and quantitative analysis of spectral data as required by the user may be utilized. Further, any optical source that provides a desired light beam 17, any interferometer 20 that provides suitable modulation of the light beam as desired by the user, any optical detector 22 that is capable of detecting the light beam after it has been reflected multiple times in the sample path by the mirror configuration 12, may be utilized as would be apparent to one skilled in the art.

In accordance with the present invention, the sample path 18 which is defined by the volume through which the modulated light beam passes in the folded path mirror configuration 12 is positioned within a sample cell enclosure 30. The sample holding compartment 14 is sealingly positioned about a sample introduction opening therein represented generally by the dashed line of FIG. 1. The sample holding compartment 14 may be of any shape or size as long as it allows for off-gases of material therein to be introduced into the sample path 18 without obstruction or interference of the light traveling in the sample path 18. For example, the sample holding compartment 14 may be a compartment smaller than the cell enclosure 30 as shown in FIG. 1, may be positioned above, below or alongside the cell enclosure 30 with an opening for introduction of the off-gases at most any point of the cell enclosure, or may be a compartment or chamber that surrounds the cell enclosure.

The sample cell enclosure 30 and structure associated therewith, as will become apparent from the detail description below, includes structure for the connection of gas control flow and measurement components for use in calibration of the apparatus 10 with standard calibration gases, i.e. calibration transfer standards (e.g., ethylene 1 ppmv) and other analysis associated functions. Such gas control flow and measurement components can include components such as a vacuum pump, mass flow controllers, compressed gases, rotometers, vacuum/pressure gauges, sample lines, feeding and safety valves, humidification systems, gas blending devices, and gas sampling devices as are known to those skilled in the art and which are commonly used in other gas analysis systems. The gas flow control and measurement components are fluidly coupled to the sample path. The description below with respect to an embodiment of the present invention shows, at least in part, some of the gas control flow and measurement components. However, as is known to one skilled in the art, various other components may be used in conjunction with the spectroscopic components of the present invention.

The apparatus 10 also includes a closed flow pump system for providing a recirculating flow between the sample holding compartment 14 and sample path 18. The closed flow pump system may include any conventional pump system and suitable gas flow lines for providing such a recirculating flow. The recirculating flow allows a representative sample of off-gasses to be introduced into the sample path 18 for analysis.

The method in accordance with the present invention utilizing the in situ infrared spectrometry apparatus 10 involves calibrating the apparatus 10 without any material being positioned in the sample holding compartment 14. After the apparatus is calibrated, one or more materials are positioned in the sample holding compartment through an access port 15. A recirculating flow 24 is then provided between the sample path 18 and sample holding volume defined by the sample holding compartment 14. Analysis of a representative sample introduced into the sample path, including off-gases from the material in the sample holding volume is initiated. Any time after the near real time analysis of the sample is performed, the material can be removed from the sample holding volume and the apparatus purged such that the apparatus can be recalibrated to determine the stability of the system.

The calibration of the apparatus 10 is typically performed in the following manner. However, one skilled in the art will recognize that various deviations from this particular calibration process are possible while still achieving the calibration objective in accordance with present invention. The apparatus 10 is first purged with a background gas, for example, dry nitrogen. Other high purity gases may also be utilized to establish a background spectrum, for example, dry air, humidified nitrogen, and humidified air. A single beam spectrum or interferogram for the background gas in the sample path 18 is collected to use as background spectrum for subsequent calibration and data collection. Single beam spectrum in an FTIR system is the Fourier transformed interferogram that represents the detector response versus wavelength (i.e. infrared frequency). The interferogram is the optical signal detector response provided to the computer system 28 and is a measurement based on the optical path difference of the modulated light beam passed through the sample path 18.

Likewise, a water reference spectrum is collected for spectral subtraction in the following manner during calibration. First, an air background single beam spectrum is collected. Second, the air background spectrum collected is operated in an active absorbance align mode. A high purity gas (the same gas used in establishing the background spectrum), such as nitrogen, is humidified, such as by bubbling the gas through a water impinger or using any other technique for humidifying a gas as known to one skilled in the art. The humidified high purity gas is then flushed through the sample path 18 until water absorbance levels closely match the ambient air water vapor levels. A single beam spectrum of the humidified high purity gas is then collected. The single beam spectrum of humidified gas is then converted to an absorbance spectrum using the high purity dry gas background spectrum previously collected. The absorbance spectrum is saved as a water reference spectrum and used for spectral substraction of sample data. Spectral substraction is performed to remove spectral interferences from water in the ambient air. Spectral subtraction of carbon dioxide in addition to water may also be required to achieve low detection limits.

Optical pathlength calibration for the system 10 is then determined quantitatively by using a calibration transfer standard (CTS). The CTS is a gas standard of a compound used to achieve and/or demonstrate suitable quantitative agreement between sample spectra and the reference spectra, i.e. reference spectra being the absorption spectra of gases with known chemical compositions recorded at a known absorption pathlength which are used in the quantitative analysis of the sample spectra. In performing optical path length calibration, the enclosed sample path is flushed with the CTS. A single beam spectrum of the CTS is collected and the single beam spectrum of CTS is converted to an absorbance spectrum using the high purity dry gas background spectrum previously collected. The CTS absorbance spectrum is quantified using a CTS reference spectrum to determine the optical path length. Various CTS, suitable for calibration, such as ethylene, carbon monoxide, and methane, are readily available from commercial gas suppliers, e.g., Scott Specialty Gases.

After the optical path length calibration is performed, calibration is completed. One or more materials are then positioned in the sample holding volume, for example, such materials may be commercial products like carpet, adhesives, tiles, etc. A recirculating system is then started to move or introduce offgases from the material into the sample path 18, or in other words, the sample path 18 is presented with a representative sample, including any off-gases from the materials. A single beam spectrum of the sample is collected. The single beam spectrum is then converted to absorbance spectra using the background spectrum previously collected. The sampled absorbance spectra is then quantified using a known reference spectrum to determine levels of the gas, gases, or off-gases present in the sample which correspond to reference spectrum for such gas, gases, or offgases at concentrations of part per million by volume (ppmv).

At the end of the process, the optical path length can once again be determined quantitatively by using the CTS with the material in the sample holding volume being removed. With the material removed from the sample holding volume, the apparatus 10 is flushed with the CTS and a single beam spectrum of the CTS is collected. The single beam spectrum of CTS is converted to an absorbance spectrum using the background spectrum previously collected. The CTS absorbance spectrum is then quantified using the CTS absorbance spectrum generated during initial calibration to determine the instrument and optical path length stability throughout the sample analysis process, from initiation to completion.

The spectrometry apparatus 10 allows ambient air to remain in the off-gassing sample holding compartment during placement of material therein and analysis. Therefore, the ambient air is periodically analyzed and a background concentration created for use in determining the off-gas compounds. Alternatively, the ambient air is removed using vacuum pumping and replaced with certified compressed cylinder gases (e.g., nitrogen or air).

The apparatus 10 is an in situ apparatus for providing near real time data for the material in the sample holding compartment being analyzed. It should be readily apparent to one skilled in the art that the apparatus 10 may be made mobile. Further, after initial calibration, the apparatus can be calibrated or recalibrated at any time upon removal of the material from the sample holding volume.

One particular embodiment of the in situ infrared spectrometry apparatus 10 utilized in the method for analysis of material off-gasses, is shown in the FIGS. 3–6. It will be readily apparent to one skilled in the art that the embodiment described herein of the in situ infrared spectrometry apparatus 10 may be configured in a number of different manners as will become apparent from the description below. However, the different configurations which may be suitable for the apparatus 10 are required to provide a folded path optical mirror configuration defining a sample path and to provide a sample holding compartment sealingly positioned with respect to the sample path. This provides the combination of an environmental chamber, i.e., a chamber for insertion of one or more materials that may produce off-gases, with a sample cell enclosure for performing in situ measurement of such off-gases.

Figure 3:
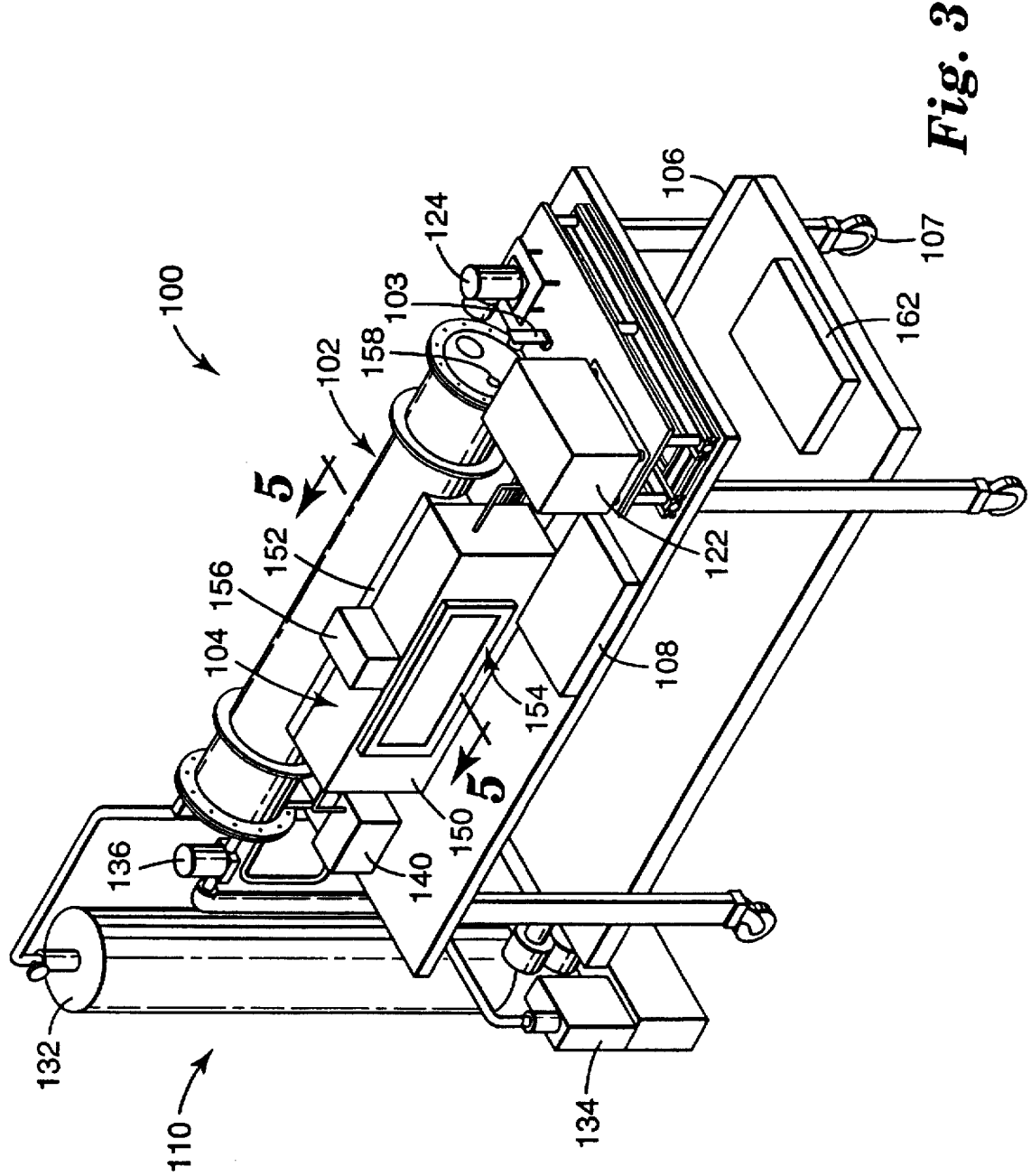
FIG. 3 is a perspective view of an embodiment of an in situ infrared spectrometry apparatus generally shown in FIG. 1 including the sample holding compartment in accordance with the present invention.

FIG. 3 is a perspective view of an in situ infrared spectrometry system 100 in accordance with the present invention. In FIG. 3, the spectrometry system 100 shows the sample holding compartment 104 sealingly positioned relative to the sample cell enclosure 102 that houses the sample path for performing analysis of gases therein. The in situ infrared spectrometry system 100 includes a movable cart 106 having wheels 107 for providing mobility to the system 100. Upon cart 106 are mounted sample cell enclosure 102 with the sealingly coupled sample holding compartment 104. Further mounted thereon are other spectrometry system components for performing gas analysis.

At one end of the sample cell enclosure 102 which is mounted to the cart 106 by brackets 103, are infrared source and interferometer 122 and infrared detector 124. The source/interferometer 122 and detector 124 are configured for transfer of light beams through respective optical windows to the sample path in the sample cell enclosure 102 by various components, such as, for example, transfer optics and laser alignment devices.

At the other end of the sample cell enclosure 102 are gas control and flow measurement devices 1 1 0. For example, such devices include an evacuation and purging pump 134 connected to a port of the sample cell enclosure 102 for evacuating or purging the sample cell enclosure and sample path therein for performance of various functions thereafter, such as calibration. Further shown is gas cylinder 132 which may contain any inert, calibration, humidification, purging gas for use in performing the various procedures utilized in gas analysis. Also shown are various valves for use in analysis procedures. Further, there are various other ports available, such as the ports 158 for adding known sample gases to the off-gases being analyzed, i.e., spike-in gases, during the analysis of the off-gases.

In addition, a DC battery source 162 may be positioned for use by the apparatus. Although the unit can be utilized with a DC battery source to make it portable, the unit may also be powered with an AC source.

Further, the system 100 includes a computer 108, preferably a DC laptop computer, for portability purposes of the system 100. Otherwise, the laptop computer 108 may be powered by AC. The laptop computer 108 includes the data collection and analysis software for controlling the analysis process and performing quantification of the data collected as previously described. There are various software packages suitable for use with spectroscopic systems.

The sample holding compartment 104 includes a main chamber 150 connected to a flow inlet section 152 which is connected to the sample cell enclosure 102 by welding or other suitable means. The main chamber 150 which defines the sample holding volume into which one or more materials are positioned, such as, with a rack, includes an access port 154.

Figure 5:
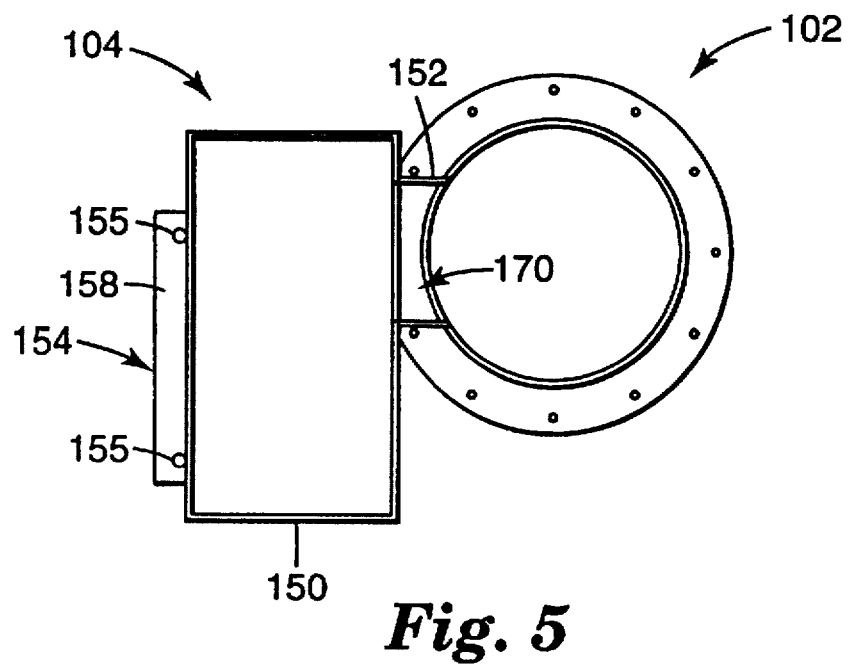
FIG. 5 is a partial schematic illustrative view of the sample holding compartment and the sample cell enclosure taken at line 5—5 as shown in FIG. 3.

As shown in the schematic view of the sample holding compartment 104 and the sample cell enclosure 102 of FIG. 5, the sample holding compartment 104 is sealingly positioned about the sample introduction opening 170 of the sample cell enclosure 102. The flow inlet section 152 is welded about the sample introduction opening 170 of the cell enclosure 102 and is shaped such that the sample path defined in the interior of the cell enclosure 102 is not disrupted, i.e., there is no interference with the light beam as it passes through the sample path. The other end of the flow inlet section 152 is connected to the main chamber 150 by welding or similar means or is sealed thereto with the use of an o-ring or other such device. The sample holding compartment 104 and sample cell enclosure 102 may be made of chemically passivated stainless steel, such as by a process available under the trade designation of SUMMA from Summa Four, Inc., Manchester, New Hampshire. Further, the compartment 104 and enclosure 102 may be of any electropolished or chemical inert material.

Figure 6:
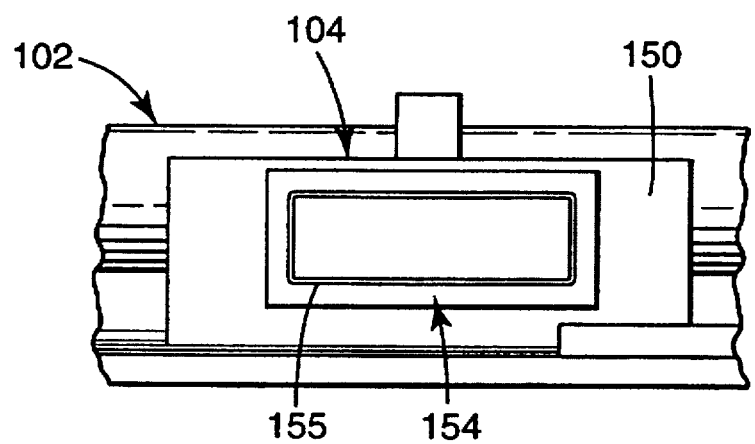
FIG. 6 is a front detailed view of the sample holding compartment and the sample cell enclosure with the access cover to the sample holding compartment removed.

The access port 154, also shown in FIG. 5 and in the front detailed view of the sample holding compartment 104 and the sample cell enclosure 102 of FIG. 6, includes an access cover 158. The access cover 158 is removed in FIG. 6, showing the o-ring seal 155. The access cover may be locked into a sealed position by any known locking technique.

Figure 4:
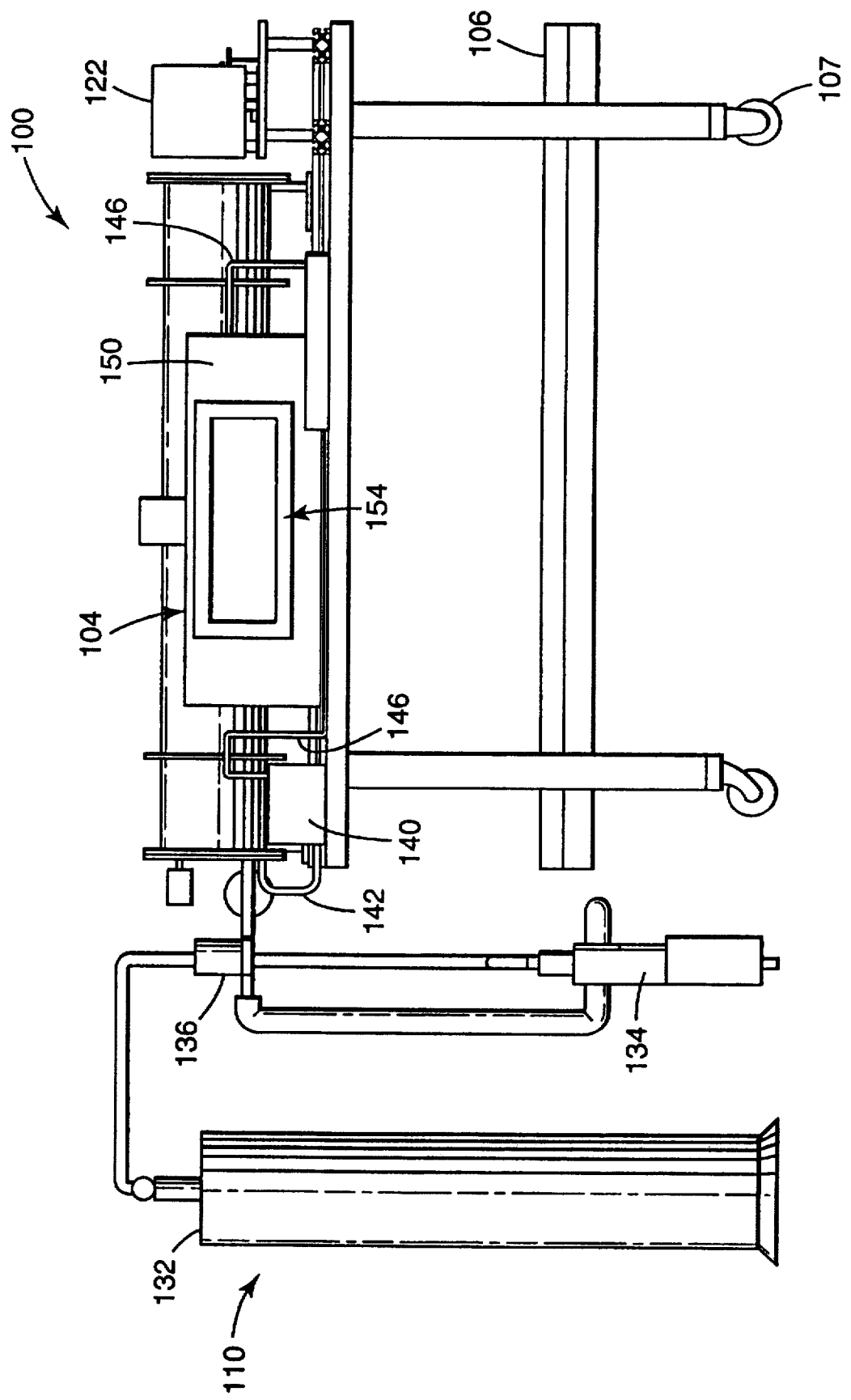
FIG. 4 is a front view of the in situ infrared spectrometry apparatus shown in FIG. 3 including the sample holding compartment in accordance with the present invention.

As shown in the FIGS. 3 and 4, the apparatus further includes a recirculating pump system. The recirculating pump system includes pump 140. Pump 140 is connected to the sample cell enclosure 102 by line 142 and to one side of the sample holding compartment 104 by line 146. In this particular embodiment, line 146 runs under the compartment 104 and connects to the far side of the sample holding compartment 104. However, connection to any portion of the compartment is contemplated in accordance with the present invention. The recirculating pump system introduces the off-gases from materials placed in the sample holding volume defined by the sample holding compartment 104 into the sample path of the sample cell enclosure 102.

Not shown in the perspective view of system 100 is the folded mirror configuration of the system. However, the mirror configuration may be any known folded path mirror configuration, and is preferably a multi-pass White cell mirror configuration as described herein. Such configurations are available from Infrared Analysis, Inc., Anaheim, Calif.

As configured, the system 100 can be operated as a combination environmental chamber and spectrometry system. This allows a representative sample of off-gases from material positioned in the sample holding volume to be introduced into the sample path and analyzed in situ. The system 100 is one embodiment of the apparatus that would be utilized in the method of analyzing off-gasses from one or more materials as described previously with respect to the present invention.

Although the system 100 is shown in a horizontal state, i.e. the sample path has a length that is parallel to the ground, it is recognized that sample cell enclosure or any other components of the system 100 may be orientated vertically and still provide the functionality in accordance with the present invention. For example, the sample holding compartment 104 may be oriented vertically relative to the length of the cell enclosure 102, the compartment may be positioned at the end of the cell enclosure as opposed to the center, or the sample compartment may be an over all enclosure completely surrounding the cell enclosure.

Moreover, the compartment may include any components for ease of insertion of materials into the sample holding volume. For example, a stainless steel rack or screen may be used to position the materials in the sample holding compartment 104. Further, the compartment may include one or more access ports.

The following example demonstrates the in situ analysis of infrared absorbing airborne chemical compounds from material off-gassing. The apparatus described above is utilized to perform the analysis without need for a sampling event from a separate conventional environmental chamber. The purpose of the example is to determine what compounds are present in the off-gas of adhesive tape samples and to determine if there is a measurable difference in the off-gas profiles of two different tape samples.

EXAMPLE 1

Two separate sample rolls from two different lots (Lot A and Lot B) of adhesive tape were analyzed using the in situ spectrometry system 100 described above with reference to FIGS. 3–6. Sub-samples of the rolls were placed into the sample holding compartment for analyses. A sub-sample consists of three strips of tape with dimensions of 6 inches by 24 inches (3 ft/sample (0.28 m$^2$/sample)). The paper backing on the tape was not removed. Representative sections of the tape had a weight determination of 14.43 g/ft$^2$ (1.34 g/m$^2$) for Lot A and of 34.22 g/ft$^2$ (3.18 g/m$^2$) for Lot B. All weights included the paper backing.

Generally, the analysis of adhesive tape off-gases determined the presence of ethyl acetate, iso-octyl acrylate, acrylic acid, methanol, toluene, and isooctyl alcohol. A summary of off-gas monitoring results are provided below in Tables 1 and 2.

TABLE 1

Determination of Off-Gas Concentration for Lot A

| Analyte | Average Concentration (ppmv) | Average Concentration (mg/ft$^2$) (based on 3.0 ft$^2$ sample) |
|---|---|---|
| Ethyl Acetate | 1.485 | 0.1922 |
| Iso-Octyl Acrylate | 0.0002 | Not Available |
| Iso-Octyl Alcohol | Not Detected | Not Detected |
| Acrylic Acid | 1.415 | 0.1499 |
| Methanol | 0.2291 | 0.0108 |
| Toluene | 2.165 | 0.2931 |

TABLE 2

Determination of Off-Gas Concentration for Lot B

| Analyte | Average Concentration (ppmv) | Average Concentration (mg/ft$^2$) (based on 3.0 ft$^2$ sample) |
|---|---|---|
| Ethyl Acetate | 2.179 | 0.2821 |
| Iso-Octyl Acrylate | 0.0001 | Not Available |
| Iso-Octyl Alcohol | 0.0001 | 0.00002 |
| Acrylic Acid | 1.735 | 0.1838 |
| Methanol | 0.5601 | 0.0264 |
| Toluene | 3.254 | 0.4404 |

Fourier transform infrared (FTIR) spectroscopy was used to identify and quantify compounds detected in the tape off-gas samples. The test was conducted using EPA protocol, U.S. EPA, "Protocol for the Use of Extractive Fourier Transform Infrared (FTIR) Spectrometry for the Analysis of Gaseous Emissions from Stationary Sources" as a guide.

Infrared spectra were collected using a MIDAC (Irvine, Calif.) FTIR system incorporated with a passivated (passivation type EPS-502, Type G; specification QQ-P-35; Mil-Spec 45208; Mil Standard 45662; performed by: Electrolurgy, Irvine, Calif.) stainless steel apparatus as described above with reference to FIGS. 3–6. The apparatus was configured with a stainless steel sample holding compartment to facilitate the introduction of and the recirculation of off-gases. The apparatus had an optical pathlength of 125–127 meters and a volume of 106 liters. The spectrometry software to acquire and manipulate data was GRAMS/386 For Windows from Galactic Industries (Salem, NH). Analyte quantification was performed using a Least Squares Fit FTIR Spectral Analysis Method provided from Rho Squared. The following provides further description of the apparatus:

Instrument: MIDAC Model M2501-C
Co-add Scans: 64
Resolution: 0.5 cm-1
Cell Temperature: 71.2–80.3° F.
Cell Pressure: 724–738 Torr
Vacuum Source: Rotary-vane pump
Calibration Standard: 1.034 and 1.029 ppmv ethylene
Reference Standard: Zero Grade Nitrogen The adhesive tape samples from the different lots were separately loaded into the sample holding compartment, the recirculating pump system was activated, and the off-gases analyzed. Sample spectra were collected at various time intervals during the off-gas equilibrium period.

Water and carbon dioxide spectral features were removed from the sample spectra collected to obtain low detection limits. To remove these spectral features, first a humidified zero nitrogen spectra that matched the ambient air water vapor concentration was created. Next, the spectra for water (humidified zero nitrogen) was manually subtracted from each sample spectra. Carbon dioxide was removed from the sample spectra using a suitable reference spectrum. With these spectral features removed, the features of the off-gas compounds were revealed and accurately quantified.

The spectrometry apparatus can allow ambient air to remain in the off-gassing chamber during the analysis. Therefore, the ambient air was periodically analyzed and a background concentration is created for use in detection of the off-gas compounds.

In general, the analytical system quality control performance was based upon the requirements set forth in U.S.

EPA, "Protocol for the Use of Extractive Fourier Transform Infrared (FTIR) Spectrometry for the Analysis of Gaseous Emissions from Stationary Sources," EMTIC Bulletin Board (3 Feb. 1995). As a closed passive system to monitor the off-gases created from a material was used, matrix spiking could be performed. The pressure in the sample cell enclosure was monitored during the analysis and pathlength was determined at the beginning and end of each analytical sequence using Ethylene (e.g., 1.034 and 1.029 ppmv) in Nitrogen Calibration Transfer Standard (CTS).

QA Soft for GRAMS'95 ethyl acetate reference spectra and 3M Company iso-octyl acrylate and iso-octyl alcohol reference spectra were used to quantify off-gas compound concentrations. In addition, HANST acrylic acid and EPA methanol and toluene reference spectra were used to quantify off-gas compounds.

All spectra were collected as "Single Beam" data. The spectrometry apparatus was evacuated to less than or equal to 10 Torr between samples.

Although the invention has been described with particular reference to preferred embodiments thereof, variations and modifications of the present invention can be made within a contemplated scope of the following claims as is readily known to one skilled in the art.

What is claimed is:

1. An apparatus for use in analyzing off-gases of a sample, comprising:

an optical source for providing an optical signal;

an optical signal detector;

a first housing which comprises a measurement volume, the first housing having folded path optical elements positioned therein, the folded path optical elements defining a sample path through which the optical signal passes, the first housing further having a sample introduction opening; and a second housing defining substantially only a sample holding volume, the second housing sealingly positioned with respect to the first housing for fluidly connecting the sample path and the measurement volume of the first housing with the sample holding volume of the second housing through the sample introduction opening, wherein the first housing and second housing form at least a portion of a sealed closed system, and further wherein the second housing includes a sealable access port through which the sample is introduced into the sample holding volume.

2. The apparatus according to claim 1, wherein the optical source is an infrared source, and wherein the folded path optical elements are White cell folded path optical elements.

3. The apparatus according to claim 1, further including means for providing a recirculating flow between the sample path and the sample holding volume.

4. The apparatus according to claim 1, wherein the sealable access port is closed with a detachable access closure.

5. The apparatus according to claim 4, wherein the first housing is a cylindrical enclosure having first and second ends for supporting the folded path optical elements and wherein the sample introduction opening is located in the cylindrical enclosure at a position between the first and second ends.

6. The apparatus according to claim 1, wherein the first housing includes means for receiving at least one gas selected from the group including calibration gas, humidified gas, purging gas, and spike-in gas.

7. The apparatus of claim 1, further comprising:

an interferometer for modifying the optical signal.

8. The apparatus of claim 7, wherein the folded path optical elements define a sample path through which the optical signal passes from the interferometer to the optical signal detector.

* * * * *